United States Patent [19]

Adkins

[11] Patent Number: 4,661,113
[45] Date of Patent: Apr. 28, 1987

[54] IMPLEMENT ATTACHMENT FOR A HANDICAPPED ARM

[76] Inventor: Charles E. Adkins, 17636 Crystal La., Milwaukie, Oreg. 97222

[21] Appl. No.: 747,945

[22] Filed: Jun. 24, 1985

[51] Int. Cl.⁴ .............................................. A61F 2/68
[52] U.S. Cl. ................................ 623/65; 273/162 R; 273/77 R
[58] Field of Search ........................ 623/65; 483/122; 273/162 R, 77 R, 67 B

[56] References Cited

U.S. PATENT DOCUMENTS

| | | | |
|---|---|---|---|
| 2,566,215 | 8/1951 | La Croix | 623/65 |
| 3,490,078 | 1/1970 | Perez | 623/65 |
| 3,747,128 | 7/1973 | De Filipo | 623/65 |
| 3,802,302 | 4/1974 | Bengston | 623/65 |
| 3,965,491 | 6/1976 | Frenzel | 623/65 |
| 4,125,905 | 11/1978 | Mitchell | 623/65 |
| 4,357,717 | 11/1982 | Puhl | 623/65 |

Primary Examiner—Richard J. Apley
Assistant Examiner—James Prizant
Attorney, Agent, or Firm—Eugene M. Eckelman

[57] ABSTRACT

A body member is attachable at one of its ends to a handicapped arm and this body member is removably attachable to a stud secured in a handle end of an implement to be manipulated. The body member includes an axially non-rotatable, universal pivot connection allowing versatile movement of the implement.

2 Claims, 6 Drawing Figures

U.S. Patent   Apr. 28, 1987   4,661,113
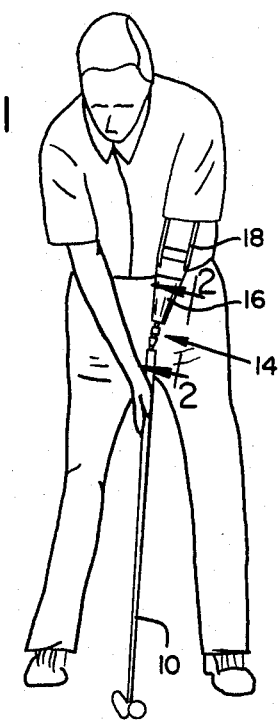
FIG.1
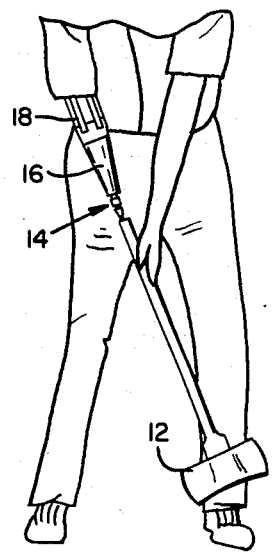
FIG.6
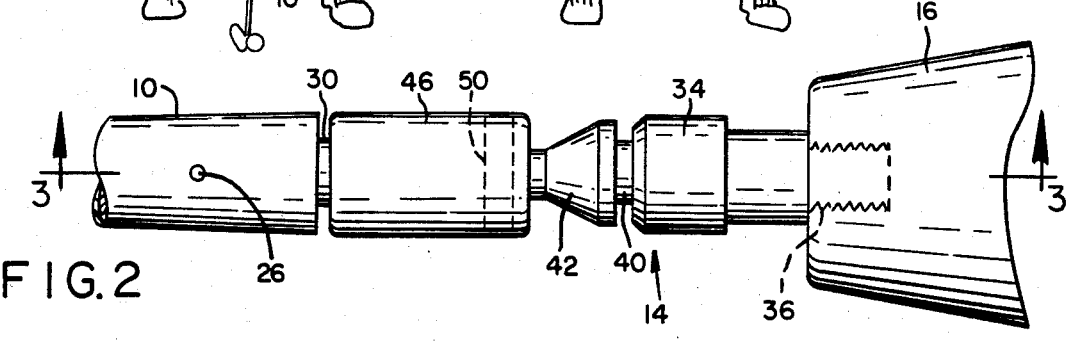
FIG.2
FIG.3
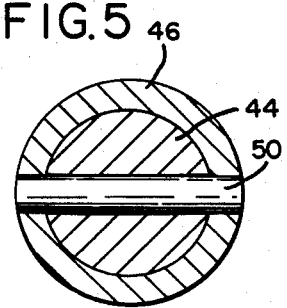
FIG.5
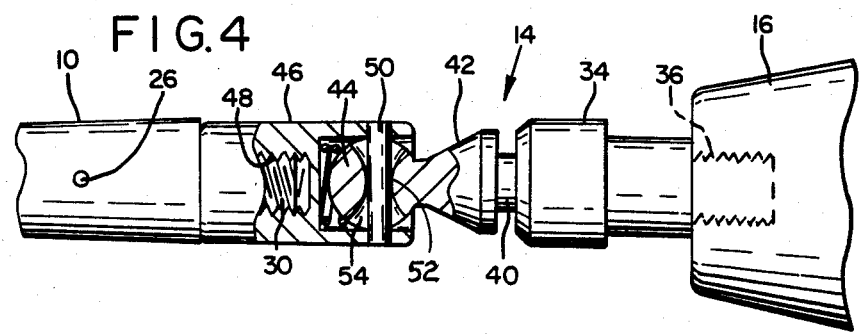
FIG.4

4,661,113

IMPLEMENT ATTACHMENT FOR A HANDICAPPED ARM

BACKGROUND OF THE INVENTION

This invention relates to new and useful improvements in an attachment for connecting implements to the handicapped arm of a person.

Various attachments have heretofore been provided for connecting implements to handicapped arms for the purpose of assisting the person in manipulating implements. For example, U.S. Pat. Nos. 3,747,128, 3,965,491 and 4,357,717 are concerned with the attachment of a golf club to a prosthetic arm or hand device. U.S. Pat. No. 2,566,215 is concerned with an adapter for attaching a tennis racket to the prosthesis.

SUMMARY OF THE INVENTION

According to the present invention and forming a primary objective thereof, an implement attachment is provided for handicapped arms which amounts to a substantial improvement in many respects over existing devices.

A more particular object of the invention is to provide an attachment of the type described which is readily adaptable for use with handicapped arms and which is readily connected and disconnected for temporary use.

Another object is to provide a device of the type described which is readily adaptable to many different types of implements.

Yet another object is to provide such a device which is simplified in construction and inexpensive to manufacture.

In carrying out the objectives of the invention, the device comprises an attachment employing a body member having securing means at one end for securement thereof to the handicapped arm. The body member has an attachment portion on the opposite end from the end which is arranged for attachment to the arm, and this attachment portion has threaded engagement with a stud member integrally attached to an implement. The body member includes a pivot joint therein and may be formed of a selected number of segments to achieve a desired extended length.

The invention will be better understood and additional objects and advantages will become apparent from the following description taken in connection with the accompanying drawings.

BRIEF DESCRIPTION OF THE DRAWINGS

FIG. 1 is a perspective view of the present invention as utilized in conjunction with a golfer amputee;

FIG. 2 is an enlarged fragmentary elevational view taken on the line 2—2 of FIG. 1;

FIG. 3 is a sectional view taken on the line 3—3 of FIG. 2;

FIG. 4 is an elevational view taken similar to FIG. 2 but broken away to show internal structure;

FIG. 5 is a cross sectional view taken on the line 5—5 of FIG. 3; and

FIG. 6 is a view similar to FIG. 1 but showing the present attachment associated with an axe as the implement.

DETAILED DESCRIPTION OF A PREFERRED EMBODIMENT

With particular reference to the drawings and first to FIGS. 1 and 6, the present invention is capable of use with various types of implements, for example a golf club 10, FIG. 1, an axe 12, FIG. 6, or other implements such as shovels and other garden tools, tennis rackets, and so forth.

The present attachment is designated generally by the numeral 14 and is shown herein in combination with a prosthesis 16 of a well known type. As will be more apparent hereinafter, the general concept of the invention can be used with various types of handicapped arms and prosthetic devices but for purposes of detail, it is illustrated in combination with a prosthetic device arranged to fit on a stump arm and having an attaching harness 18 engageable with the shoulder and neck. This type of prosthesis has a nut 20, FIG. 3, on the terminal end thereof for connection to artificial hands, etc. of known construction.

In accordance with the invention, the implement to be used, for example, a golf club 10, FIG. 1, is equipped with a stud 24 in the end of the handle. This stud is securely attached in place such as by a cross pin 26 and also by epoxy 28 if desired. Stud 24 is mounted in the implement in a position such that a threaded end 30 thereof projects from the end of the handle. Most golf clubs have a hollow handle 32, and the stud 24 is readily mounted therein. In the case of other implements, such as an axe 12 or other implements, it will be necessary to drill a hole in the end of the handle for receiving the stud.

The present invention comprises a body member which is arranged for connection between the nut 20 of the prosthesis 16 and the threaded end 30 of the stud 24. For this purpose, the body member comprises an adapter 34 having a threaded end projection 36 arranged for removable threaded engagement with the nut 20 of the prosthesis. Adapter 34 has a threaded socket 38 on the end opposite from the end 36, and this socket is engageable by a threaded end projection 40 on a stem 42 terminating at the opposite end in a ball portion 44. This ball portion is received within a socket member 46 having an end threaded recess 48 removably engageable with the threaded end 30 of the stud 24.

Ball portion 44 and socket 46 are connected together in a spring-pressed universal limited joint by a cross pin 50. This pin passes through a center aperture 52, FIG. 4, in the ball 44, the latter having tapered recesses 54 leading from the aperture 52 to allow a certain amount of universal pivotal movement of the stem 42 in the socket 46, namely, with reference to FIG. 4, the club can swing to and from the viewer, it can pivot at right angles to the cross pin, or it can pivot in a combination of these two. Such a combination allows the said certain amount of universal pivotal movement but not total universal movement. The particular cut-out of recesses 54 and the pivotal movement around the axis of the pin as seen in FIG. 4 allows a sufficient amount of universal movement for the intended purpose. The pin 50 prevents axial rotation, however. The stem 42 and socket member 46 have a selected engaged relation such that the stem can pivot only a selected distance, for example, 45 degrees from the axis of the socket portion. Further pivoting of the stem is prevented since it will engage the end edge of the socket 46. The purpose of such limited movement prevents excess breaking of these two parts, such restriction being beneficial for some uses, as for example, a backswing check-point for the golf club as will be more apparent hereinafter. The pin 50 while allowing said uiversal pivotal movement of the ball, prevents said axial rotation of the stem 42.

In the use of the present device, the implement is first provided with the stud 24. In the case of a set of golf clubs, each club is provided with its own stud. Upon threadedly connecting the implement to the prosthesis, a secured connection between these two members is established and it is readily apparent that this connection to the stump arm will greatly assist in operation of the implement. The harness portion 18 of the prosthesis 16 will generally not allow a normal or full backswing but the universal pivot connection 44, 46, will allow the golfer to bring the club back farther in order to increase the backswing for attaining greater power. At the same time, the abutment of the stem 42 against the socket 46 will limit over extending the backswing.

In some cases, the adapter 34 may not be necessary as a part of the present device, namely, in those cases where its length is not needed. The stem 42 can then be directly connected to the prosthesis. In this regard, the threaded end 40 is constructed to fit the nut 20.

It is also within the concept of the invention to utilize other connecting means than that shown for attaching the device to the arm of a handicapped person. For example, it may be desired to provide a faster connect and disconnect to the prosthetic device or to the implement. Common snap-in structures may be adapted for this purpose. Where great tension forces are present, however, such as for golf and chopping with an axe, a positive non-slip connection such as screw threads is desired. It is also within the invention to utilize strap or other connecting means which provide attachment to an arm or hand that has been weakened or disabled by disease or accident. The device can also be adapted as a training tool for normal, two handed golfers.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. An attachment arranged for connection between an implement of the type having a handle portion with a free end and an arm prosthesis mounted on a stump arm and having thread means at its free end for releasable securement to an implement, said attachment comprising:

stud means arranged to be secured in an opening at one end of an implement for permanent installation and having a threaded end arranged to project beyond the end of the implement, a socket member, said socket member including two parts each with opposite ends.

one of said parts having said first threaded securing means on one end thereof and a ball on the other end, the other of said parts having said second threaded securing means on one end and a socket receiving said ball on the other end, a central aperture in said ball having outwardly tapered recess portions, and a cross pin secured in said socket member extending freely through said central aperture providing pivotal connection of said socket member around said pin as well as allowing some pivotal movement in said recesses on an axis at right angles to said cross pin but at the same time preventing rotation of said socket member on its longitudinal axis; wherein the threaded end of the second part of said socket member is releasably connected to the threaded end of the stud means, and the threaded end of the first part of said socket member is releasably connected to an adapter means which itself is threadably attached to the free end of an artificial arm.

2. In combination, a golf club having a head end and a hollow round grip end, stud means installed integrally in said hollow end of said golf club and having a threaded end projecting from said handle, a body member having the opposite ends, first securing means on one end of said body member arranged to secure said body member releasably to the securing means of an arm prosthesis as an extension of the latter, and second securing means on the other end of said body member securing it releasably to said stud means installed in said golf club, said body member including two parts pivotally connected together in a limited universal pivotal but axially non-rotatable connection.

* * * * *